United States Patent [19]

Crutcher et al.

[11] 3,940,491

[45] Feb. 24, 1976

[54] BACTERIAL SOURCE OF VITAMIN K FOR ANIMAL FEEDS

[75] Inventors: Richard E. Crutcher, Waukegan; Victor W. Winkler, Libertyville, both of Ill.

[73] Assignee: Abbott Laboratories, North Chicago, Ill.

[22] Filed: Apr. 25, 1975

[21] Appl. No.: 571,828

[52] U.S. Cl. .......... 426/2; 426/61; 426/72; 426/807
[51] Int. Cl.² .......... A23K 1/00; A23L 1/30
[58] Field of Search .......... 426/2, 61, 72, 807; 195/DIG. 9

[56] References Cited
UNITED STATES PATENTS

| | | | |
|---|---|---|---|
| 3,079,260 | 2/1963 | Galler | 426/72 X |
| 3,079,261 | 2/1963 | Berruti | 426/72 |
| 3,196,018 | 7/1965 | Galler | 426/72 |
| 3,328,169 | 6/1967 | Nanninga | 426/72 X |

*Primary Examiner*—James R. Hoffman
*Attorney, Agent, or Firm*—Gildo E. Fato; Robert L. Niblack

[57] ABSTRACT

The vitamin K is produced by bacteria which are a mixture of normal gastrointestinal flora which are fermented, spray dried and added to a feed supplement. The use is mainly for poultry but could be used also on other animals.

5 Claims, 3 Drawing Figures

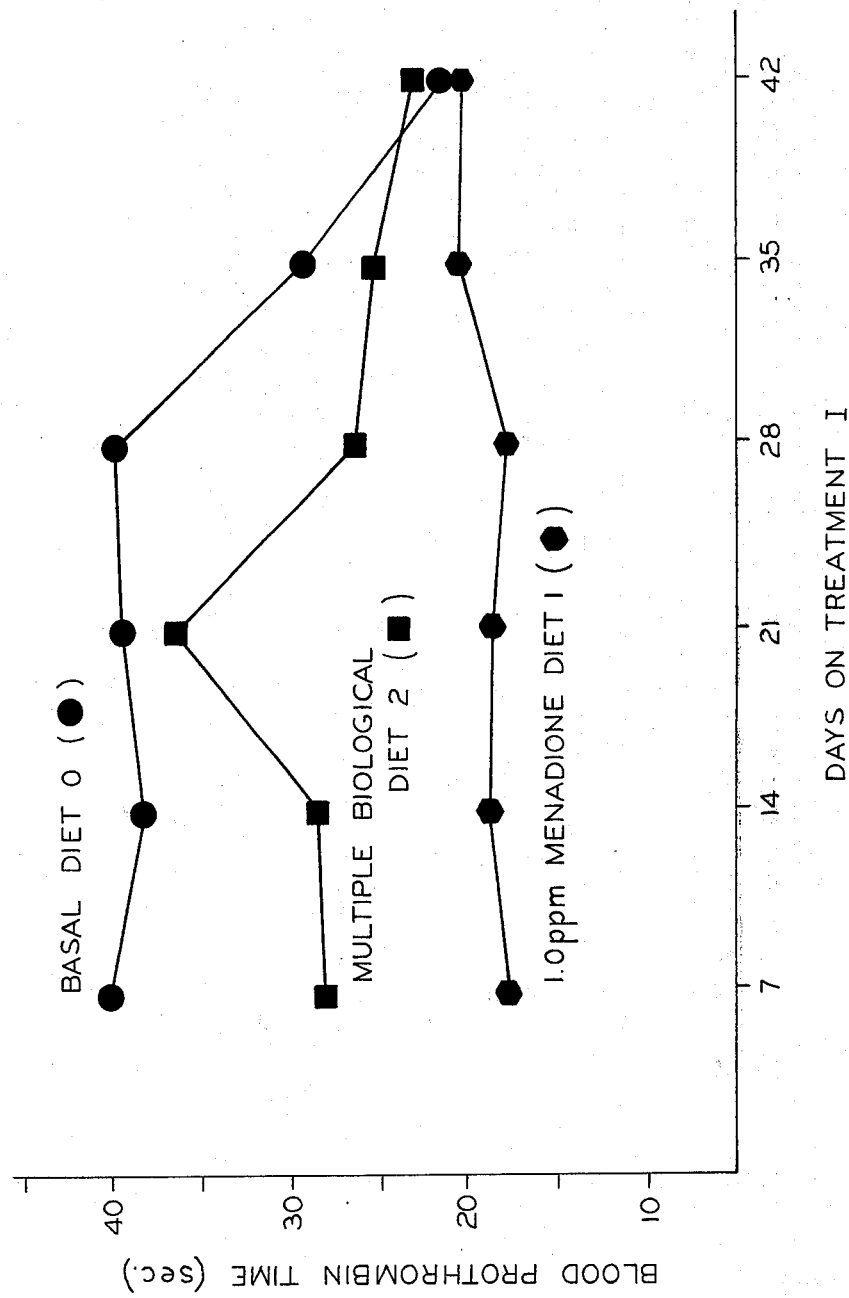

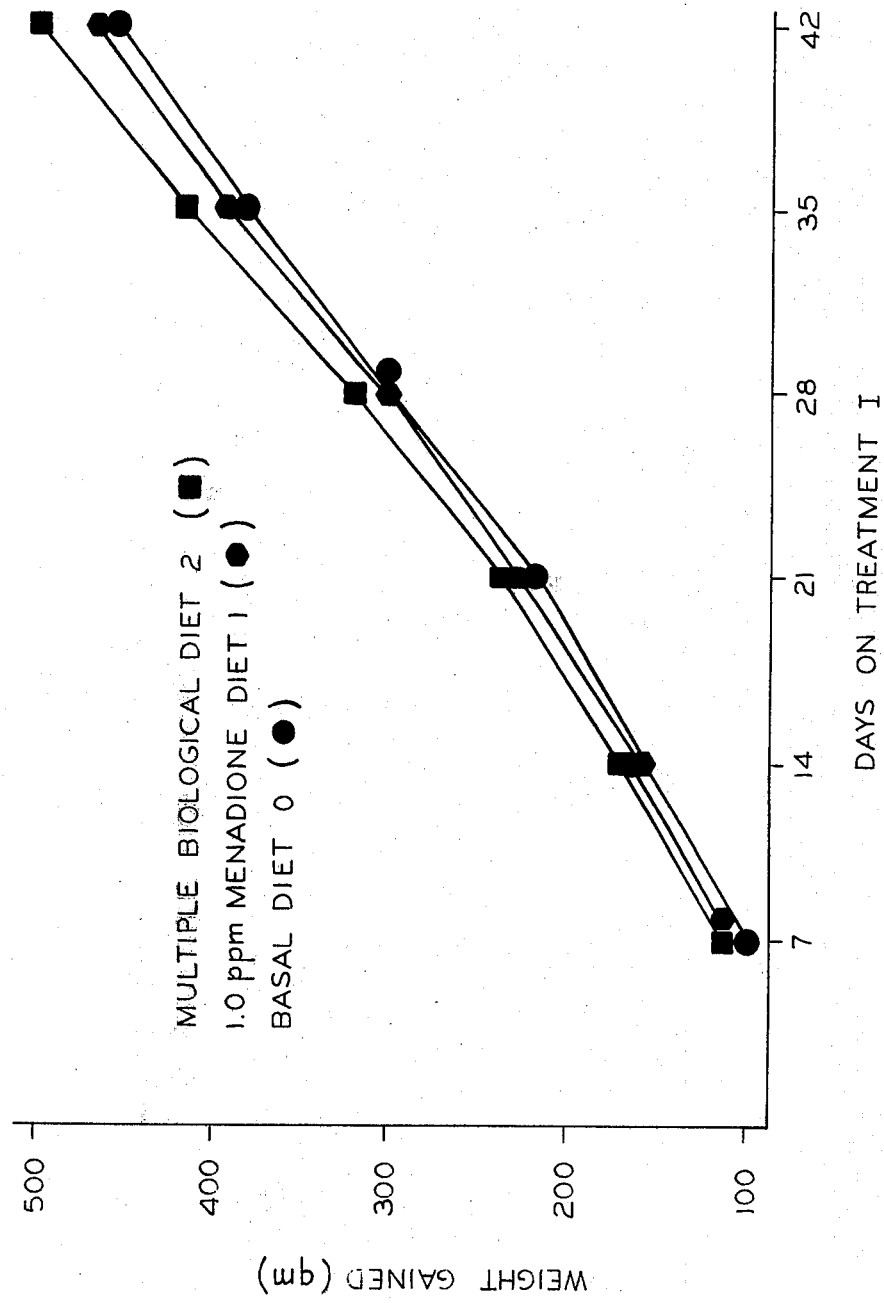

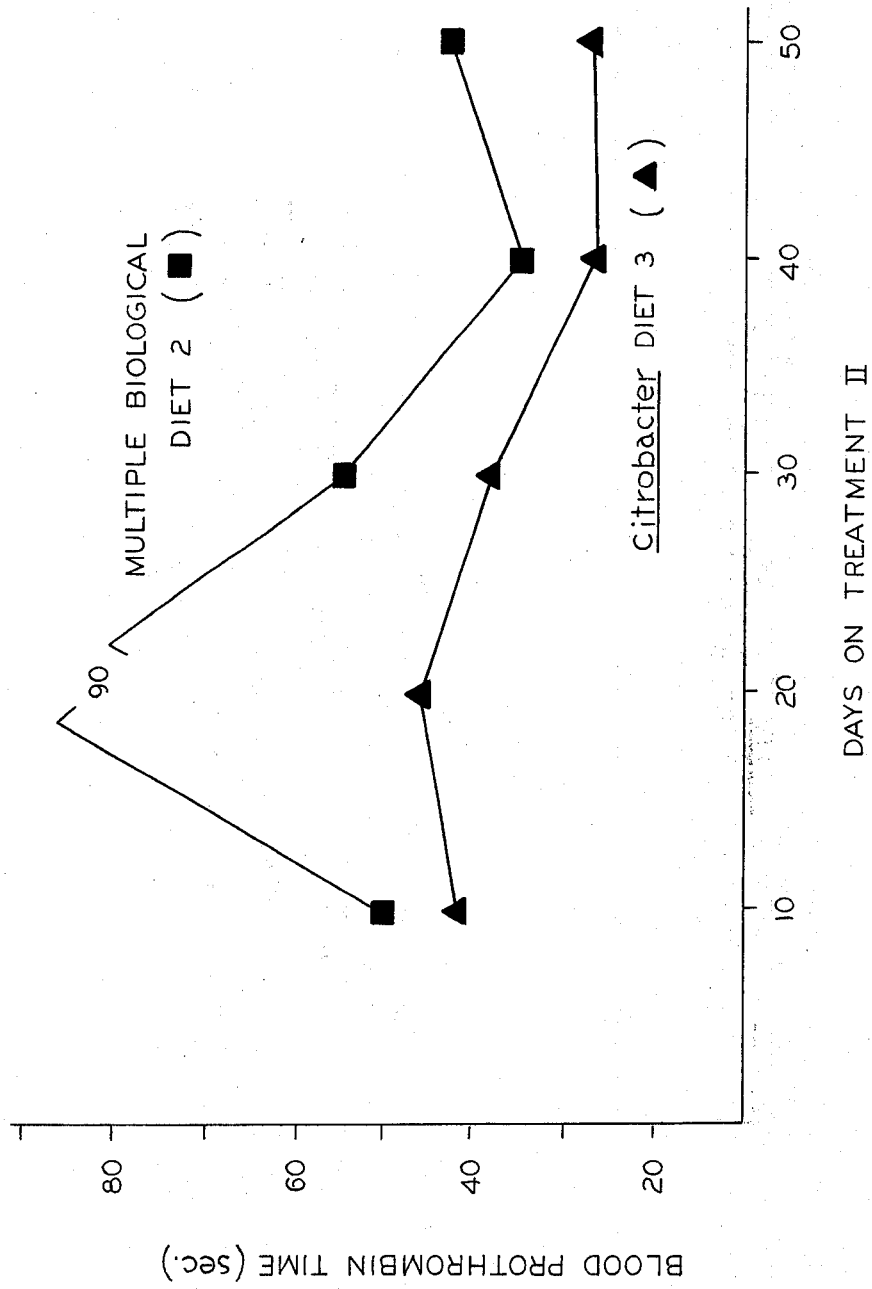

BACTERIAL SOURCE OF VITAMIN K FOR ANIMAL FEEDS

This invention relates to vitamin K, and more particularly to a bacterial source of vitamin K which is mixed with animal feed to give a yound animal an internal source of vitamin K.

In a nutritional deficiency of vitamin K, chicks show a hemorrhagic syndrome characterized by internal bleeding and long blood clotting time. A severely affected bird may bleed to death as a result of pulling out a pin feather. In rats and other species it is difficult to produce a deficiency by feeding rations void of the vitamin. Such species are supplied with the vitamin from intestinal bacteria which synthesized it. The microorganisms are decomposed in part, and the vitamin thus becomes available for absorption. This also occurs normally in human beings.

Regardless of the way in which a deficiency is produced, the end result is a lowering of the blood plasma prothrombin. If this becomes severe, blood clotting time is lengthened and various manifestations of the hemorrhagic syndrome may ensue. The liver requires the vitamin for the synthesis of prothrombin. That vitamin K may interact with tissue cells seems clear since no amount of it has been demonstrated to affect the coagulation of normal or of K deficient blood in vitro. Vitamin K serves as prosthetic group for the APO enzyme required for the mechanism involved in prothrombin synthesis.

A new born infant is subject to the elementary vitamin K deficiency since the vitamin is not readily passed from mother to fetus. The disease is characterized by low prothrombin levels, and consequently, a tendency to hemorrhage. Often a spontaneous abatement of this tendency ensues, as a result probably of establishment of intestinal flora in the infant.

It is suggested that a bacterial source of vitamin K would be more efficacious than any of the presently available forms of vitamin K supplements. Mixed with animal feeds, the bacteria would give the young animal an internal source of vitamin K. The feasibility of this approach is supported by past literature. (The Bacteria 1962, I. C. Gunsalus and R. Y. Stainer)

The presently available product exhibits an exceedingly poor stability (e.g. 90 to 95% loss during pelleting) and cannot account for the level of prothrombin activity observed in chickens after five to six weeks diet of a given feed.

The recommended bacteria is a mixture of normal gastrointestinal flora consisting of non-pathogenic strains of clostridia, escherichia, aerobaster, microbacteria, and enterobacteriacease. A mixture is desirable as even non-pathogens can produce disease under optimum conditions (i.e. no growth competition). The mixture is fermented as a single batch with chicks to ensure proper growth of all organisms. The final beer can be spray dried and mixed with feed at levels to be sold either as a premix or as a final feed.

Since the primary intention of this feed is to ensure the early presence of intestinal flora, the loss of a percentage of the organism during any special treatment of the feed (such as pelleting) should be inconsequential.

A spontaneous appearance of vitamin K activity as measured by blood prothrombin clotting times were shown to occur at four to five weeks of age with chicks fed a low vitamin K diet. A "multiple biological" supplemented feed, prepared from cultured chick intestinal microorganisms, let into a low vitamin K diet fed to five day old chicks was shown to maintain nearly normal blood clotting time indicating biological induction of vitamin K activity. A "single biological" supplemented feed was prepared using the microorganism, Citrobacter isolated from the "multiple biological" supplement, and shown to be a major contributor for the in vivo induction of vitamin K activity in chicks.

The following examples will serve to illustrate the methods used and the results obtained in the present invention.

EXAMPLE I

SOURCE I. A "multiple biological" feed supplement cultured by incubating the fluid contained in the first 10 cm. of intestine (duedeno-jejunal flexure) following the proventrichulus of a six-week old Leghorn hen in fluid thioglycolate broth for 48 hours at 32°C. The organisms present after incubation were isolated by centrifugation, washed with sterile distilled water, and mixed with a small amount of zein before drying under vacuum at room temperature. Bacterial identification tests (API-20 System for the Identification of Enterobacteriacease, Analytab Products, Inc., N.Y., N.Y.) revealed the presence of the following four types of organisms: *Klebsilla pneumoniae*, *Streptococcus faecalus*, *Streptococcus liquifaciens*, and *Citrobacter*.

EXAMPLE II

SOURCE II. A "single biological" feed supplement, was prepared from isolated Citrobacter in a manner similar to that described above.

Test Ration Preparation

Test diets were prepared as follows: Diet 0, a basal ration (void of vitamin K and containing 0.1% sulphaquinoxaline as a vitamin K antagonists); Diet 1, basal ration supplemented with menadione bisulfite and chemically assayed, to initially contain 1 ppm equivalence menadione; Diet 2, basal ration supplemented with "multiple biological" Source I and biologically assayed to contain $10^4$ organisms per gm; Diet 3, basal ration supplemented with "single biological" Source II and biologically assayed to contain $10^4$ Citrobacter organisms per gm.

Animal Treatment

Two separate treatments were used in this study as described below:

Treatment I. Eighteen 5-day old female Leghorn chicks which had been feeding on a commercial chick starter (high in alfalfa content) were divided into three groups of six and placed on each of the following diets; basal ration (Diet 0), menadione bisulfite supplement ration (Diet 1), or "multiple biological" supplemental ration (Diet 2). Blood prothrombin clotting times (BPC) were determined at one week intervals.

Treatment II. Sixteen 1-day old female Leghorn chicks were divided into two groups of eight and placed on the "multiple biological" supplemented ration (Diet 2) or the Citrobacter "single biological" supplemented ration (Diet 3). BPC times were determined at ten day intervals as described above.

The chicks were kept in wire floor batteries and fresh water was supplied daily throughout both treatments.

Evaluation of Treatment I

A comparison of both BPC times and weight gains was made each week for six successive weeks with the five day old chicks placed on the basal ration (Diet 0), menadione bisulfite ration (Diet 1), or "multiple biological" ration (Diet 2).

The blood prothrombin clotting times (BPC) for the chicks placed on Treatment I (basal, menadione bisulfite, and "multiple biological" rations) are presented in Table 1. The chicks on Diet 1 containing the synthetic vitamin K supplement maintained normal BPC times at ca. 20 seconds throughout the six week intervals. The chicks after one week on Diet 0, the vitamin K deficient basal reaction, showed an increase in BPC times from ca. 20 seconds to 40 seconds and maintained that BPC level through week four. Normally, chicks maintained only on a low K diet will have BPC times greater than 80 seconds. The chicks on Treatment I, however, were not severely stressed because they had been on a commercial chick starter high in alfalfa content for five days prior to being placed on the test diets. This probably accounts for the lower than expected BPC times observed for chicks on the basal and "multiple biological" rations.

As shown in Table I, the BPC times of the chicks fed the low K diet (containing no supplements) dropped from ca. 40 seconds at week four to 21 seconds at week six indicating availability of vitamin K which quite likely was a result of intestinal microflora development. Additional evidence indicating the significance of available natural vitamin K via microflora is seen with the chicks fed the multiple biological ration (Diet 2). Nearly normal BPC times were observed (28.4 to 23.3 sec.) with this group throughout the six week interval with exception of the 36.5 seconds at week three. The relatively low BPC times (ca. 28 sec.) for this group for the first two weeks on test could be attributed to natural vitamin K already present in the microorganisms, but there appears to be little doubt that after week four on the test diet (where the chicks are at five weeks of age) additional available vitamin K is being produced by the intestinal flora and made available to the chicks. A graphic representation of the results of Treatment I is presented in FIG. 1.

A graph of the weight gains observed with Treatment I is shown in FIG. 2. It is apparent that with respect to weight gain coupled with the fact that no mortalities were observed, the chicks on the multiple biological ration (Diet 2) suffered no adverse effects. Indeed, although the differences were not statistically significant, the weights of the chicks on Diet 2 consistently were higher than the control vitamin K supplemented Diet 1.

Evaluation of Treatment 2

A comparison of BPC times was made during every ten successive days for 49 days with the one day old chicks placed on either the "multiple biological" ration (Diet 2) or the Citrobacter ration (Diet 3).

BPC times for the chicks placed on Treatment II (multiple biological and Citrobacter single biological rations) are shown in FIG. 3. Placement of 1-day old chicks on the test diets in Treatment II resulted in more stress relative to Treatment I. For this reason the BPC times of the chicks on the "multiple biological" ration (Diet 1) increased from 50 seconds at 10 days to greater than 90 seconds at 20 days on test as compared to BPC times not being greater than ca. 40 seconds in Treatment I. However, the BPC times of chicks on the Citrobacter ration (Diet 3) ranged from about 35 to 40 seconds throughout the first 30 days on test. It is clearly seen that the presence of Citrobacter has maintained blood clotting capabilities of the chicks and is probably the main source and/or producer of natural vitamin K in the intestinal microflora which is available to the chicks. After 30 days on test, indication of increased vitamin K activity is seen with both test Diet 2 and Diet 3 and after 40 days on tests nearly normal BPC times are observed with the Citrobacter supplemented Diet 3.

In conclusion, it appears that biological induction of vitamin K activity occurs in chicks between four to five weeks of age and that Citrobacter is the major contribution towards this phenomenon.

TABLE I

| | BLOOD PROTHROMBIN CLOTTING TIME OF CHICKS on TREATMENT I[a] | | |
|---|---|---|---|
| | BLOOD PROTHROMBIN CLOTTING TIME (Sec.) ± Coef. Var.[b] | | |
| Week/Diet | Basal Diet 0 | Menadione Bisulfite Diet 1 | Multiple Biological Diet 2 |
| 1 | 40.5 ± 8.5 | 17.7 ± 10.7 | 28.3 ± 14.8 |
| 2 | 38.4 ± 5.6 | 18.7 ± 12.2 | 28.4 ± 19.6 |
| 3 | 39.5 ± 24.6 | 18.7 ± 10.5 | 36.5 ± 8.5 |
| 4 | 39.9 ± 8.9 | 17.5 ± 12.8 | 26.1 ± 8.5 |
| 5 | 29.4 ± 14.6 | 20.4 ± 2.7 | 25.3 ± 6.6 |
| 6 | 21.2 ± 14.6 | 20.4 ± 4.2 | 23.3 ± 7.3 |

[a]Chicks were placed on test diets after five days feeding on a commercial chick started high in alfalfa content.
[b]Each value represents an average of five chicks.

What is claimed is:

1. A method for maintaining a proper level of vitamin K in animals comprising the steps of mixing a bacterial source of said vitamin K with an animal's feed and feeding said mixture to an animal.

2. The method of claim 1 wherein said bacterial source is Citrobacter.

3. The method of claim 1 wherein said bacterial source is *Klebsilla pneumoniae*.

4. The method of claim 1 wherein said bacterial source is *Streptococcus faecalus*.

5. The method of claim 1 wherein said bacterial source is *Streptococcus liquifaciens*.